United States Patent [19]

Kristiansen et al.

[11] 4,163,056
[45] Jul. 31, 1979

[54] PESTICIDAL TRIAZAPENTADIENES

[75] Inventors: Odd Kristiansen, Möhlin; Dieter Dürr, Bottmingen, both of Switzerland

[73] Assignee: Ciba-Geigy Corporation, Ardsley, N.Y.

[21] Appl. No.: 945,673

[22] Filed: Sep. 25, 1978

[30] Foreign Application Priority Data

Sep. 29, 1977 [CH] Switzerland ............... 11911/77

[51] Int. Cl.² ................ A01N 9/20; C07C 125/08
[52] U.S. Cl. .................... 424/324; 260/551 C
[58] Field of Search ............... 260/551 C; 424/324

[56] References Cited

U.S. PATENT DOCUMENTS

| | | | |
|---|---|---|---|
| 3,225,077 | 12/1965 | Schaefer et al. | 260/551 C |
| 3,875,230 | 4/1975 | Pissiotas | 260/564 RF |
| 3,898,277 | 8/1975 | Duerr et al. | 424/324 |
| 4,115,583 | 9/1978 | Böger et al. | 424/324 |

Primary Examiner—Dolph H. Torrence
Attorney, Agent, or Firm—Harry Falber

[57] ABSTRACT

Triazapentadienes of the formula

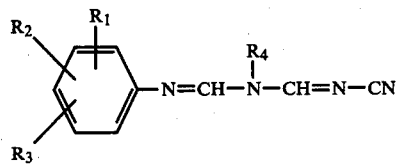

in which $R_1$, $R_2$ and $R_3$ are each hydrogen, halogen, $C_1$-$C_3$ alkyl or trifluoromethyl, and $R_4$ is $C_1$-$C_4$ alkyl, processes for producing them and their use in controlling pests.

7 Claims, No Drawings

PESTICIDAL TRIAZAPENTADIENES

The present invention relates to triazapentadienes and salts thereof with inorganic and organic acids, to processes for producing them and to their use in controlling pests.

The said triazapentadienes have the formula

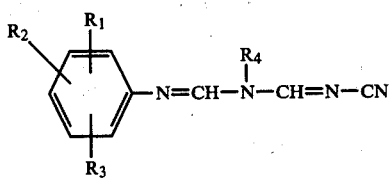

in which $R_1$, $R_2$ and $R_3$ are each hydrogen, halogen, $C_1$-$C_3$ alkyl or trifluoromethyl, and $R_4$ is $C_1$-$C_4$ alkyl.

By halogen in this case is meant fluorine, chlorine, bromine or iodine.

Alkyl groups denoted by $R_1$, $R_2$ and $R_3$ can be straight-chain or branched-chain. Examples of such groups are, inter alia: methyl, ethyl, propyl, isopropyl and n-, i-, sec- or tert-butyl.

Suitable for forming salts are inorganic acids such as HCl, $H_2SO_4$, HBr and $H_3PO_4$; and organic acids suitable for this purpose are for example saturated and unsaturated mono-, di- and tricarboxylic acids, such as formic acid acetic acid, oxalic acid, phthalic acid, succinic acid and citric acid.

Compounds of the formula I preferred on account of their action are those in which $R_1$ and $R_2$ are each chlorine, bromine, methyl or trifluoromethyl, $R_3$ is hydrogen and $R_4$ is methyl.

The triazapentadienes of the formula I can be produced by processes known per se, for example by reacting a compound of the formula

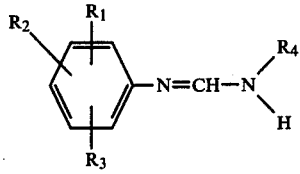

in which $R_1$ to $R_4$ have the meanings given under the formula I, with the compound of the formula

$$C_2H_5O-CH=N-CN$$

The process is performed at a temperature of 0° to 120° C., preferably between 20° and 100° C., under normal or elevated pressure, and in an inert solvent or diluent.

Suitable solvents or diluents are, for example: ethers and ethereal compounds such as diethyl ether, dipropyl ether, dioxane, dimethoxyethane and tetrahydrofuran; amides such as N'N-dialkylated carboxylic acid amides; aliphatic, aromatic as well as halogenated hydrocarbons, especially benzene, toluene, xylene, chloroform and chlorobenzene; nitriles such as acetonitrile; dimethylsulfoxide and ketones such as acetone and methyl ethyl ketone. The process can also be performed in an aqueous solution.

The starting materials of the formula II are known and can be produced by known processes. The compounds of the formula I are suitable for controlling various animal and plant pests. The compounds possess nematocidal properties and can be used for example for controlling phytopathogenic nematodes. They are also suitable for combating viruses, bacteria and phytopathogenic fungi.

The compounds of the formula I are suitable in particular for the control of insects, of phytopathogenic mites and of ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

Compounds of the formula I are especially suitable for controlling insects which damage plants, particularly insects which damage plants by eating, in crops of ornamental plants and productive plants, especially in cotton crops (for example against Spodoptera littoralis and Heliothis virescens) and in vegetable crops (for example against Leptinotarsa decemlineata and Myzus persicae). The active substances of the formula I also have a very favourable action against flies, such as Musca domestica, and against mosquito larvae.

The acaricidal and insecticidal action can be substantially broadened and adapted to suit given circumstances by the addition of other insecticides and/or acaricides. Suitable additives are, for example, organic phosphorus compounds; nitrophenols and derivatives thereof; formamidines, ureas; pyrethrin-like compounds, and also carbamates and chlorinated hydrocarbons.

Compounds of the formula I are combined particularly advantageously also with substances having an intensifying effect. Examples of such compounds are, inter alia: piperonyl butoxide, propynyl ethers, propynyl oximes, propynyl carbamates and propynyl phosphonates, 2-(3,4-methylenedioxyphenoxy)-3,6,9-trioxaundecane and S,S,S-tributylphosphorotrithioates.

The compounds of the formula I can be used on their own or together with suitable carriers and/or additives. Suitable carriers and additives may be solid or liquid, and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

Solid preparations:
dusts, scattering agents or granulates (coated granules, impregnated granules and homogeneous granules);

Liquid preparations:
(a) water-dispersible concentrates of active substance: wettable powders, pastes or emulsions;
(b) solutions.

The content of active substance in the described compositions is between 0.1 and 95%.

The active substances of the formula I can be formulated, for example, as follows:

DUSTS

The following substances are used to produce (a) a 5% dust and (b) a 2% dust:
(a) 5 parts of active substance, and 95 parts of talcum; and
(b) 2 parts of active substance, 1 part of highly dispersed silicic acid, and 97 parts of talcum.

The active substance is mixed and ground with the carriers.

GRANULATE

The following ingredients are used to produce a 5% granulate:
5 parts of active substance
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin, and the acetone is subsequently evaporated off in vacuo.

WETTABLE POWDERS

The following constituents are used to produce
(a) a 40%, (b) and (c) a 25%, and (d) a 10% wettable powder:
(a) 40 parts of active substance, 5 parts of sodium lignin sulfonate, 1 part of sodium dibutyl-naphthalene sulfonate, and 54 parts of silicic acid;
(b) 25 parts of active substance, 4.5 parts of calcium lignin sulfonate, 1.9 parts of Champagne chalk/hydroxyethyl cellulose mixture (1:1), 1.5 parts of sodium dibutyl-naphthalene sulfonate, 19.5 parts of silicic acid, 19.5 parts of Champagne chalk, and 28.1 parts of kaolin;
(c) 25 parts of active substance, 2.5 parts of isooctylphenoxy-polyethylene-ethanol, 1.7 parts of Champagne chalk/hydroxyethyl cellulose mixture (1:1), 8.3 parts of sodium aluminium silicate, 16.5 parts of kieselgur, and 46 parts of kaolin;
(d) 10 parts of active substance, 3 parts of a mixture of the sodium salts of saturated fatty alcohol sulfates, 5 parts of naphthalenesulfonic acid/formaldehyde condensate, and 82 parts of kaolin.

The active substance is intimately mixed in suitable mixers with the additives, and the mixture is then ground in the appropriate mills and rollers to give wettable powders which can be diluted with water to obtain suspensions of the desired concentration.

EMULSIFIABLE CONCENTRATES

The following substances are used to produce (a) a 10%, (b) a 25% and (c) a 50% emulsifiable concentrate:
(a) 10 parts of active substance, 3.4 parts of epoxidised vegetable oil, 3.4 parts of a combination emulsifier consisting of fatty alcohol polyglycol ether and alkylarylsulfonate calcium salt, 40 parts of dimethylformamide, and 43.2 parts of xylene;
(b) 25 parts of active substance, 2.5 parts of epoxidised vegetable oil, 10 parts of an alkylarylsulfonate/fatty alcohol polyglycol ether mixture, 5 parts of dimethylformamide, and 57.5 parts of xylene; and
(c) 50 parts of active substance, 4.2 parts of tributylphenol-polyglycol ether, 5.8 parts of calcium-dodecylbenzenesulfonate, 20 parts of cyclohexanone, and 20 parts of xylene.

Emulsions of the concentration required can be prepared from these concentrates by dilution with water.

SPRAY

The following constituents are used to produce (a) a 5% spray and (b) a 95% spray:
(a) 5 parts of active substance, 1 part of epichlorohydrin, and 94 parts of ligroin (boiling limits 160°–190° C.); and
(b) 95 parts of active substance, and 5 parts of epichlorohydrin.

The invention is further illustrated by the Examples which follow.

EXAMPLE 1

A solution of 5 g of ethoxymethylenecyanamide is added dropwise at room temperature to a solution of 8.1 g of N-methyl-N'-(2,4-dimethylphenyl)-formamidine in 50 ml of absolute dioxane. The reaction mixture is stirred for two hours and the substance which has precipitated is filtered off and washed with ether. There is thus obtained the compound of the formula

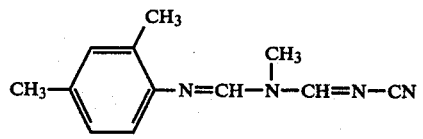

having a melting point of 170°–171° C. The following compounds are produced in an analogous manner:

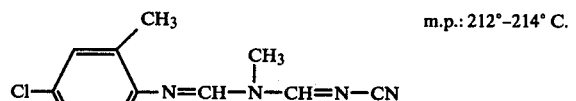

m.p.: 212°–214° C.

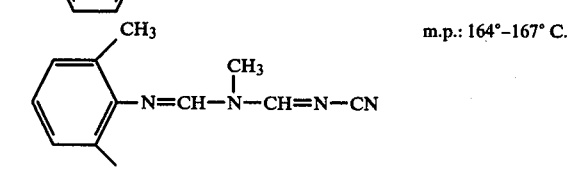

m.p.: 164°–167° C.

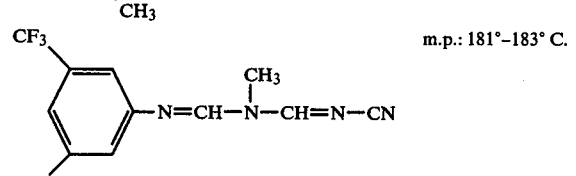

m.p.: 181°–183° C.

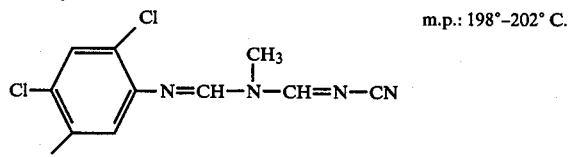

m.p.: 198°–202° C.

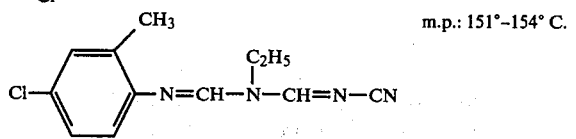

m.p.: 151°–154° C.

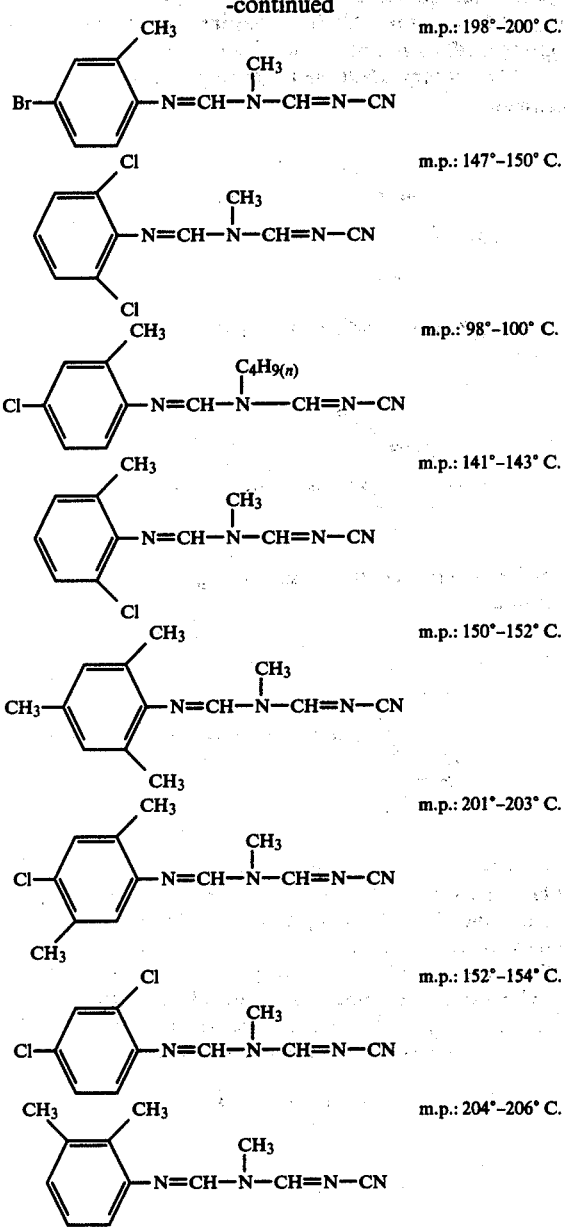

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the $L_3$-stage and of *Heliothis virescens* in the $L_3$-stage were placed onto the cotton plants. The test was carried out at 24° C. with 60% relative humidity.

Compounds according to Example 1 exhibited in the above test a good insecticidal stomach-poison action against larvae of Spodoptera littoralis and Heliothis virescens.

(B) Systemic insecticidal action

In order to determine the systemic action, rooted bean plants (*Vicia faba*) were placed into a 0.01% aqueous solution of the active substance (obtained from a 10% emulsifiable concentrate). After 24 hours, bean aphids (*Aphis fabae*) were placed onto the parts of the plants which had been above the soil. By means of a special device, the bean aphids were protected from the effects of contact and of gas. The test was carried out at 24° C. with 70% relative humidity.

Compounds according to Example 1 exhibited in the above test a systemic insecticidal action against Aphis fabae.

EXAMPLE 3

Action against *Chilo suppressalis*

Rice plants of the Caloro variety were planted, six plants per pot, in plastic pots having an upper diameter of 17 cm, and were grown to a height of about 60 cm. Infestation with *Chilo suppressalis* larvae ($L_1$; 3–4 mm long) was carried out 2 days after application of the active substance in granular form (amount applied =8 kg of active substance per hectare) to the paddy water. An evaluation of the insecticidal action was made 10 days after application of the granules.

Compounds according to Example 1 exhibited in the above test a good action against *Chilo suppressalis*.

EXAMPLE 4

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified tests preparations from a chromatography-sprayer in a manner ensuring no overflow of the spray liquor. An assessment was made after 2 to 7 days, by examination under a binocular microscope, of the living and of the dead larvae, adults and eggs, and the results were expressed as percentages. The treated plants were kept during the "holding time" in greenhouse compartments at 25° C.

Compounds according to Example 1 exhibited in the above test a good action against adults, larvae and eggs of *Tetranychus urticae*.

EXAMPLE 5

Action against soil nematodes

In order to test their action against soil nematodes, the active substances were added to soil infested with root-gall nematodes (*Meloidogyne arenaria*), and intimately mixed with the soil. In one test series, tomato seedlings were planted immediately after preparation of the soil in the manner described, and in the other test series tomatoes were sown after a waiting time of 8 days. An assessment of the nematocidal action was made by counting the galls present on the roots 28 days after planting and sowing, respectively.

Active substances according to Example 1 exhibited in this test a good action against *Meloidogyne arenaria*.

EXAMPLE 6

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 7

Action against *Erysiphe graminis* on *Hordeum vulgare*

Barley plants about 8 cm in height were sprayed with a spray liquor (0.05% of active substance) produced from wettable powder of the active substance. The treated plants were dusted after 48 hours with conidia of the fungus. The infested barley plants were placed in a greenhouse at about 22° C., and the fungus infestation was assessed after 10 days.

Compounds according to Example 1 were effective in this test against *Erysiphe graminis*.

I claim:

1. A triazapentadiene of the formula

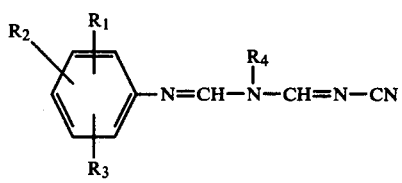

in which $R_1$, $R_2$ and $R_3$ are each hydrogen, halogen, $C_1$–$C_3$ alkyl or trifluoromethyl, and $R_4$ is $C_1$–$C_4$ alkyl.

2. A triazapentadiene according to claim 1, in which $R_1$ and $R_2$ are each chlorine, bromine, methyl or trifluoromethyl, $R_3$ is hydrogen and $R_4$ is methyl.

3. The triazapentadiene according to claim 2 of the formula

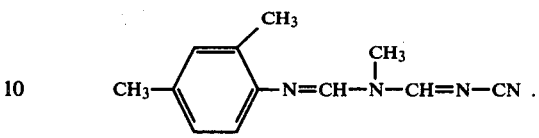

4. The triazapentadiene according to claim 2 of the formula

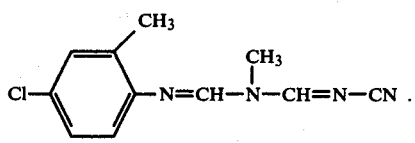

5. The triazapentadiene according to claim 2 of the formula

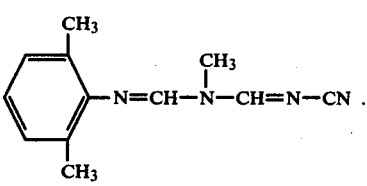

6. A pesticidal composition which comprises a pesticidally effective amount of a triazapentadiene according to claim 1 as active ingredient, and suitable carriers and/or other additives.

7. A method of combatting pests of the class Insecta or of the order Acarina at a locus, which method comprises applying to the locus an insecticidally or acaricidally effective amount of a compound as claimed in claim 1.